United States Patent [19]

Weisbart et al.

[11] Patent Number: 5,034,316
[45] Date of Patent: Jul. 23, 1991

[54] IN VITRO HUMAN MONOCLONAL IGG RHEUMATOID FACTOR AUTOANTIBODY

[75] Inventors: Richard H. Weisbart, Los Angeles; Romaine E. Saxton, Venice, both of Calif.

[73] Assignee: The Regents of the University of California, Berkeley, Calif.

[21] Appl. No.: 32,294

[22] Filed: Mar. 30, 1987

[51] Int. Cl.$^5$ .................... G01N 33/577; C07K 15/28
[52] U.S. Cl. .................................. 435/7.24; 530/387; 530/808; 435/240.27; 435/172.2; 436/548; 935/100; 935/110
[58] Field of Search ............ 435/240.27, 240.2, 172.2, 435/68, 7, 948; 530/387, 808; 436/548, 536, 542, 509; 935/100, 104, 110

[56] References Cited

PUBLICATIONS

Steinitz, M. et al., "In Vitro-produced Monoclonal Rheumatoid Factor: Purification, Radiolabeling, and Possible Applications". *Cell. Immunol.* 69(2): 205-14, 1982, as cited in Chemical Abstracts, accession no. CA97(3); 21886m.

Pope, R. M. et al. "The Molecular Basis of Self-Association of Antibodies to IgG (Rheumatoid Factors) in Rheumatoid Arthritis," *Proc. Nat. Acad. Sci.* 71(2): 517-521, Feb. 1974.

*Primary Examiner*—Esther L. Kepplinger
*Assistant Examiner*—Susan L. Futrovsky
*Attorney, Agent, or Firm*—Cooley Godward Castro Huddleson & Tatum

[57] ABSTRACT

Human monoclonal IgG RF is provided in stable supply from immortalized cells. The IgG RF can be used for diagnosis and study of rheumatoid arthritis. In addition, anti-idiotype antibodies can be provided for use in diagnosis and therapy.

The cell line hRF-1 was deposited at the A.T.C.C. on January 16, 1991 and given accession No. ATCC 10645.

3 Claims, No Drawings

IN VITRO HUMAN MONOCLONAL IGG RHEUMATOID FACTOR AUTOANTIBODY

TECHNICAL FIELD

The subject invention is concerned with the preparation in vitro of human rheumatoid factor and its use in the diagnosis and therapy of rheumatoid arthritis.

BACKGROUND OF THE INVENTION

Rheumatoid arthritis is a chronic destructive autoimmune disease associated with anti-immunoglobulins of the IgM, IgG, and IgA isotype. These antiglobulins are called rheumatoid factors (RF) because they are found at high levels in serum from rheumatoid arthritis (RA) patients. These antibodies are found to bind to the Fc portion of the patients' own Ig molecules.

Some IgM RF bind to only denatured IgG and are present in many non-rheumatoid disorders such as chronic infections, liver disease, neoplasia, and aging. These IgM RF are therefore not useful as definitive diagnostic tests for rheumatoid arthritis. They are speculated to serve as a mechanism for removal of circulating immune complexes and denatured IgG in all of the above disease conditions.

On the other hand, IgG RFs in rheumatoid arthritis patient serum appear to be true autoantibodies, since they self associate and produce pathogenic immune complexes. Little information is available on the function and specificity of autoimmune IgG RF. Inability to identify the particular autoantibodies has greatly impeded efforts to understand the etiology of the disease and to treat the disease. There is, therefore, substantial interest in finding ways to investigate the disease and understand the mechanism by which it operates, as well as finding methods to diagnose and treat the disease, particularly holistic methods to treat the disease.

DESCRIPTION OF THE RELEVANT LITERATURE

Illustrative publications concerning the characteristics of rheumatoid arthritis sera and their ability to bind to the Fc protion of the patients own IgG molecules may be found in Waller, Acta, *Path. Microbiol. Scand.* (1940) 17:172–188: Rose et al., *Proc. Soc. Exp. Biol. Med.* (1948) 68:1–6: Franklin et al., *J. Exp. Med.* (1957) 105:425–438: Lospalluto and Ziff, *J. Exp. Med.* (1959) 110:169–186: Kunkel et al., *J. Clin. Invest.* (1961) 40:117–129: and Heimer and Lavin, *Immunochemistry* (1966) 3:1–10. Discussions concerning IgM RF may be found in Twomey et al., *Proc. Natl. Acad. Sci. USA* (1976) 73:2106–2108 and Kunkel et al., *Arthritis Rheum.* (1958) 1:289–296. Pope et al., *Proc. Natl. Acad. Sci. USA* (1974) 71:517–521 suggests that the IgG RF are the true autoantibodies, since they self-associate and can produce pathogenic immune complexes. Owen et al. (Abstract) *Arthritis Rheum.* (Supplement) (1986) 29:S73 suggests the IgG RF in rheumatoid arthritis is primarily of the IgG$_4$ subclass. Thaso, ibid. (1986) 29:S73 indicates that the binding site of IgG RF is near the immunoglobulin Fc binding region of Staphylococcal protein-A (SpA). Gililand et al., *Arthritis and Rheumatism* (1978) 21:330–336 report production of an IgG RF from a cell line from the synovium of a rheumatoid patient. Pope and McDuffy *J. Lab. Clin. Med.* (1981) 97:842–853 report the analysis of various species of IgG binding to RF in an RIA. See also, Nardella et al., *J. Exp. Med.* (1985) 162:1811–1824 and Nardella et al., *J. of Immunol.* (1987) 138:922–926

SUMMARY OF THE INVENTION

Monoclonal human IgG rheumatoid factor is provided together with immortalized B-lymphocytes producing the IgG rheumatoid factor. The IgG rheumatoid factor finds use in diagnosing rheumatoid arthritis and providing for anti-idiotype antibodies, which anti-idiotype antibodies may find use as diagnostic and therapeutic agents.

DESCRIPTION OF THE SPECIFIC EMBODIMENTS

Human monoclonal IgG and particularly IgG$_4$, rheumatoid factors are provided in substantially pure form (>95% monospecificity), which are produced by a stable cell line capable of a continuous stable production of the IgG rheumatoid factor. The IgG rheumatoid factor may be $\kappa$ or $\lambda$, particularly $\kappa$. The human monoclonal IgG rheumatoid factor is further characterized by binding to human, rabbit, mouse, and guinea pig IgG with greater affinity than to horse, goat, and sheep IgG and not at all to chicken IgG. The binding pattern is similar to the species-specific binding of Staphylococcal protein-A (SpA) to the same IgG immunoglobulins. Thus, the subject monoclonal IgG rheumatoid factor appears to have the same binding pattern as SpA indicating that the subject composition and SpA may bind to the same or an overlapping site. The subject rheumatoid factor does not bind to human serum albumin, bovine collagen, histone 2A, or denatured DNA.

The subject rheumatoid factor may be obtained by immortalizing rheumatoid arthritis synovial lymphocytes from freshly prepared tissue. After digesting the tissue to remove nucleic acids and connective tissue, the B-lymphocytes which are present may be immortalized by any convenient means. Particularly, the B-lymphocytes may be immortalized by Epstein-Barr virus transformation. Alternative techniques include fusion with human myeloid cells, heteromyeloma cells, or the like. See, for example, U.S. Pat. Nos. 4,172,124 and 4,574,116 and Olsson and Kaplan, *Proc. Natl. Acad. Sci. USA* (1980) 77:5429–5431. The particular manner in which the source of the genetic capability for producing the antibodies is immortalized is not a significant aspect of the subject invention.

The immortalized cell line may then be cloned by repetitive limiting dilution and the culture supernatants screened for IgG RF autoantibody. Conveniently, human Fc may be employed as the ligand, where the Fc may be labeled or may be bound to a support and the binding of the antibodies to the Fc determined by a protein specific for human immunoglobulin or immunoglobulin complexes, e.g. SpA, C1q, etc.

The subject monoclonal antibodies may be used in a variety of ways. They may be used as immunogens for immunizing a wide variety of hosts, e.g. mice, rats, primates, etc., for the production of anti-idiotype antibodies. The immunization may follow conventional techniques employed for the production of monoclonal antibodies. Conveniently, the subject rheumatoid factor may be injected intraperitoneally, intravascularly, subcutaneously, or the like, with or without an adjuvant. Administrations may be at two-week intervals or greater intervals. Depending upon the nature of the host, a few days after the last injection, the host may be sacrificed, the spleen isolated and used as a source of the lymphocytes for immortalization. Conveniently, with mice, rats, rabbits, or the like, the lymophocytes may be immortalized by fusion employing a convenient fusogen, e.g., polyethylene glycol, under selective conditions where only the fused cells will survive. To ensure monoclonality, the cells are then cloned under limiting dilution conditions and the supernatants screened for the presence of anti-idiotype antibodies in conventional ways. For example, the subject human RF may be employed as the ligand, either labeled or used in conjunction with labeled antibodies to human immunoglobulin (hIg). Once the clones have been identified, they may be recloned under limiting dilution conditions to ensure the substantial absence of any other producing hybridoma. The monoclonal hybridomas may then be cultured or used for producing ascites fluid in an appropriate host.

The anti-idiotype antibodies may then be used for diagnosis and therapy. For diagnosis, the anti-idiotype antibodies may be used in any of the conventional assays which will be described subsequently. For therapy, the anti-idiotype may be used for passive administration to a rheumatoid arthritis patient to inhibit self-complexing of the rheumatoid factor.

The amount that will be administered will be within the conventional amounts employed for passive immunization, there being from about 10 to 500 mg/kg of host, more usually from 50 to 250 mg/kg of host. Administration may be by any convenient means, usually being administered by intravascular injection. The peptides will usually be formulated in a physiologically acceptable medium, e.g., PBS, saline, aqueous ethanol, etc.

In order to avoid an immune response to the anti-idiotype antibodies that are produced in other than the host species to be treated, e.g. other than human, the Fab fragment may be employed or the F(ab')$_2$ fragment may be employed. Alternatively, nucleic acid techniques may be employed for isolating the gene encoding the light and heavy chains of the anti-idiotype and modifying them in accordance with conventional ways to join the variable regions to human constant regions. See, for example, Oi and Morrison, *BioTechniques* (1986) 4:214–231, and references cited therein.

The variable region of the subject monoclonal antibodies may be synthesized and the synthetic sequence which cross-reacts with the variable region, particularly the hypervariable region, used as a vaccine. Usually, the synthesized sequence will be at least 12 amino acids, more usually at least 16 amino acids, and may be up to about 90 amino acids, usually not more than about 60 amino acids. The cross-reacting sequence may be joined to other immunogenic sequences by fusion, or covalent bonding using a variety of wellknown bifunctional compounds, e.g., glutaraldehyde, maleimidobenzoic acid, methyldithiopropionic acid, etc. Immunogens include proteins from various pathogens or non-primate species.

Synthesis may be achieved employing commercially available synthesizers. The synthesizers employ a solid support to which a functionalized spacer is bound. Partially blocked amino acids are added incrementally, followed by deblocking and adding the next blocked amino acid. After completion of the peptide, the peptide is removed from the support, isolated and purified, e.g., HPLC.

Alternatively, the cross-reacting peptide may be prepared by genetic techniques. All of the variable region or only a portion thereof lacking the C region, e.g., the V region, V-D region, or the V-D-J region, or a portion thereof may be obtained as cDNA by conventional techniques. The hybridoma would be used as a source of mRNA. The mRNA would be reverse transcribed using reverse transcriptase and the second strand prepared using a DNA polymerase and the dsDNA used to prepare a library.

The IgG could be partially sequenced and probes prepared using these sequences. Thus, the mRNAs for the light and heavy chains could be detected. Alternatively. the cDNA library could be subtracted with mRNA from a different hybridoma which would serve to concentrate the mRNAs encoding the subject IgG. These mRNAs could then be screened using Xenopus oocytes for proteins cross-reactive with the subject IgG. In this manner, the specific mRNAs could be identified and used to prepare cDNA.

The cDNAs could be sequenced and the region of interest synthesized in conventional ways. Alternatively, the cDNA may be manipulated by resection, in vitro mutageneses, restriction, primer repair, or the like, to provide the fragment of interest. During the various manipulations the DNA will be cloned and amplified in a convenient prokaryotic vector, e.g., pUC-X, pBR322, M13mp-X (where X intends any of the available vectors). Other techniques are also known, such as the use of λgt10 or −11 for screening a fused product with antibodies for detection of the desired sequence.

Once the DNA sequence encoding the desired sequence has been prepared, it may be used for expression by inserting the sequence in the direction of transcription downstream from a transcriptional initiation region or promoter. Various expression vectors are commercially available or published in the literature. The DNA sequence may be manipulated to include or remove the natural signal sequences replacing the leader sequence with an initiation codon. If desired, the sequence may be modified by adding one or more amino acids to serve as a linking group or fusing the sequence involving the variable region to another DNA sequence encoding an immunogen. The cross-reactive sequence could be the sequence from the heavy chain, the light chain or the covalently or noncovalently bound complex of the two variable regions. In some situations, a chimeric Ig could be prepared using a mouse or other non-primate constant region as the immunogen. Usually, the heavy chain will be selected for joining to another sequence, by itself, or in combination with the light chain. Alternatively, the heavy and light variable regions may be fused together usually with a bridging group of about 1 to 100 amino acids.

The resulting variable region peptide may be used as a vaccine to stimulate the production of anti-id antibodies to protect against rheumatoid arthritis. The vaccine will be employed substantially as described for passive immunozation except that more than one administration may be given, usually not more than three, and conventional adjuvants added, such as BCG, aluminum hydroxide, etc.

For diagnostic tests, the subject rheumatoid factors may be used as standards for the determination of the presence of rheumatoid factor in serum. The rheumatoid factor may be confirmed with a sample and the effect on the rate of agglutination of the sample determined. Erythrocytes, latex particles or other particles may be employed. In addition, the rheumatoid factors may be employed as reagents for binding to Fc in competitive inhibition assays. Anti-idiotypes may be used directly for binding to the IgG rheumatoid factor which may be present in human serum.

A wide variety of assays, either competitive or noncompetitive, are described in the literature using a variety of labels. The labels include radioisotopes, enzymes, particles, e.g. magnetic particles, glass particles, latex particles, carbon particles, etc., fluorescent molecules, e.g., fluorescein, umbelliferone, phybcobiliproteins, rhodiamine, etc., chemiluminescers, enzyme substrates, cofactors inhibitors, etc. Illustrative references describing these various techniques include U.S. Pat. Nos. 3,654,090, 3,817,837, 3,935,074, 4,134,792, 4,160,645, 4,192,983, 4,208,479, 4,275,149 and 4,341,865. The manner of conjugation of the antibody to the label is conventional, there being a wide variety of techniques described in the above literature.

For diagnosis, the antibodies may be provided as kits, where the antibodies are included with other reagents necessary for the determination. Particularly, for enzyme assays, the other reagents may include necessary substrates and cofactors, protein stabilizers, buffers, salts, biocides, and the like.

For therapy, the antibodies may be formulated in a variety of physiologically acceptable media, such as deionized water, distilled water, phosphate buffered saline, saline, aqueous ethanol, or the like. The anti-idiotype antibody may be present in concentrations from about 10 to 500 mg/kg of host. Other additives which may be included include protein stabilizers, salts, buffers, or the like.

The following examples are offered by way of illustration and not by way of limitation.

EXPERIMENTAL

Preparation of Immortalized Cell Line Secreting IgG Rheumatoid Factor

Human synovium from rheumatoid arthritis patients was obtained at the time of surgery for joint replacement. The inflammatory cell population containing $10^7$ to $10^8$ lymphoid cells was freed from stroma by digesting synovial tissue with DNAse and collagenase. The B-lymphocytes in the cell population were transformed with Epstein-Barr virus according to the method of Cole et al., *Molecular and Cellular Biochemistry* (1984) 62:109. The culture supernatant from one of ten transformed lymphoblastoid synovial primary cell cultures, hRF-1, produced detectable levels of IgG RF autoantibody by two weeks after EBV transformation. The IgG RF was detected by an enzyme-linked immunosorbent assay (ELISA) using purified human IgG Fc fragments bound to 96 well microtiter plates (Weisbart et al., *J. Immunology* (1984) 132:2909–2912). Bound IgG RF was identified with peroxidase labeled rabbit antibodies specific for the F(ab')$_2$ of human IgG. After repeated cloning, these hRF-1 B-lymphoblastoid cells secreted only IgG (1–2 μg/ml), but not IgA (less than 20 mg/ml), or IgM (less than 10 mg/ml).

Isotype testing with subclass specific antiglobulins identified only human IgG$_4$ subclass γ heavy chains. Anti-light chain specific antiglobulins detected only κ, but not λ, light chains. Initial specificity of this IgG$_4$ RF for human immunoglobulin was demonstrated by its binding to purified Fc fragments of human IgG, but not human serum albumin, bovine collagen, histone 2A, or denatured DNA, as shown in the following table.

TABLE 1

Characterization and Binding Specificity of hRF-1 Monoclonal Rheumatoid Factor by ELISA*

| | alpha | gamma | mu | | |
|---|---|---|---|---|---|
| Isotype | 0.00 | 0.60 | 0.00 | | |
| | $IgG_1$ | $IgG_2$ | $IgG_3$ | $IgG_4$ | |
| IgG subclass | 0.06 | 0.00 | 0.00 | 0.38 | |
| | kappa | lambda | | | |
| Light chain | 0.47 | 0.00 | | | |
| | Albumin | Collagen | Histone | DNA | IgG-Fc |
| Antigen binding | 0.00 | 0.04 | 0.05 | 0.03 | 1.07 |

*The human monoclonal antibody hRF-1 was bound to 96-well microtiter plastic plates at 1 μg/100 μL and characterized by ELISA using peroxidase conjugated antisera specific for human immunoglobulin isotypes, IgG subclasses, and light chains. The antigenic specificity of hRF-1 monoclonal was measured with the 5 antigens bound to 96-well microtiter plates at 1 μg/100 μL by adding hRF-1 at 2 μg/ml from culture media and detecting bound hRF-1 with affinity purified peroxidase-conjugated sheep antibodies specific for F(ab')$_2$ of human IgG. Results were recorded as absorbancy at 414 nm corrected for background values using control ELISA wells coated only with poly-L-lysine.

The hRF-1 human monoclonal IgG$_4$ RF was tested for binding to different species IgGs and shown to bind to human, rabbit, mouse, and guinea pig IgG more strongly than to horse, goat, and sheep IgG. The monoclonal IgG$_4$ RF did not bind at all to chicken (nonmammalian) IgG. The observed binding pattern is analogous to the species-specific binding of Staphylococcal protein-A (SpA). SpA at concentrations as low 1 μg/ml in direct competitive binding assays with hRF-1 monoclonal IgG RF for the ability to react with human IgG Fc resulted in a 30% inhibition of this low concentration, whereas equimolar concentrations of another Fc binding protein, complement factor C1q did not inhibit binding of the hRF-1 monoclonal IgG to human IgG Fc.

RA patient sera was tested for the similarity between SpA and hRF-1 monoclonal IgG RF. Results showed the presence of IgG RF in 6/6 RA sera with the same binding pattern to mammalian IgG as to hRF-1 monoclonal IgG RF. In contrast, this binding pattern was not present in serum with IgG RF to human IgG Fc obtained from three patients with bacterial endocarditis, two patients with systemic lupus erythematosus and one patient with gout.

Preparation of Anti-id (hRf-1)

Balb/c mice are each immunized with 0.05 to 0.10 mg hRF-1 in 0.2 ml PBS and boosted intravenously one week later with 0.05 mg hRF-1. Three days after the booster injection the spleen cells are fused with mouse myeloma cells (a nonsecreting clone of P3x63AG8) in 50% polyethyleneglycol 1540. The fused cells are put in 96-well tissue culture plates and the hybrids selected conventionally with HAT medium. After 3 weeks, supernatants are tested by RIA using $^{125}$I-hRF-1 as the ligand (Zelter and Super. *J. Immunol. Methods* 1977) 17:163 and Nowinski et al., *Virology* (1979) 93111). One clone anti-id (hRF-1) is selected by binding to hFR-1 but not to IgG$_4$ Fc, and inhibiting binding of hRF-1 to Fc, and grown to subconfluency in a microtiter well. The cells are transferred to Leighton tubes and expanded in tissue culture flasks. Aliquots of cells are cloned by limiting dilution. The cells are grown in culture medium and the monoclonal anti-id (hRF-1) IgG isolated in accordance with conventional ways.

It is evident from the above results that the subject invention provides a continuous stable source of IgG RF which can be used in the study of rheumatoid arthritis, for the production of anti-idiotype antibodies and in diagnostic assays. The anti-idiotype antibodies may also find use in diagnosis and therapy, detecting the presence of IgG RF and aiding in the elimination of IgG RF in a rheumatoid arthritis patient.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. Human monoclonal IgG rheumatoid factor hRF-1 monoclonal antibody ATCC 10645.

2. A method for determining the presence of rheumatoid factor in a blood sample, said method comprising:
    combining a human monoclonal IgG rheumatoid factor according to claim 1 with said blood sample; and
    determining the change in rate of self-complexing as a result of the presence of said blood sample as compared to a standard having a known amount of rheumatoid factor.

3. A labeled human monoclonal IgG rheumatoid factor, wherein said human monoclonal IgG rheumatoid factor is hRF-1 monoclonal antibody ATCC 10645.

* * * * *